US007163711B2

(12) United States Patent
Nishimoto et al.

(10) Patent No.: US 7,163,711 B2
(45) Date of Patent: Jan. 16, 2007

(54) CRYSTALLINE α-D-GLUCOSYL α-D-GALACTOSIDE, SACCHARIDE COMPOSITION COMPRISING THE SAME, PROCESS FOR PRODUCING THE SAME, AND USES THEREOF

(75) Inventors: Tomoyuki Nishimoto, Okayama (JP); Michio Kubota, Okayama (JP); Shigeharu Fukuda, Okayama (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 776 days.

(21) Appl. No.: 10/455,730

(22) Filed: Jun. 6, 2003

(65) Prior Publication Data

US 2003/0228404 A1    Dec. 11, 2003

(30) Foreign Application Priority Data

Jun. 6, 2002    (JP)    ............................ 2002/166299
Jan. 17, 2003   (JP)    ............................ 2003/009056
May 8, 2003     (JP)    ............................ 2003/129801

(51) Int. Cl.
*A23G 3/00*    (2006.01)

(52) U.S. Cl. ...................... 426/658; 127/58; 127/61; 536/123.13

(58) Field of Classification Search ................ 426/548, 426/658; 536/4.1, 123, 123.13, 124; 127/58, 127/61; 435/193
See application file for complete search history.

(56) References Cited

U.S. PATENT DOCUMENTS 5,441,644 A  *  8/1995  Kinouchi .................... 210/651
5,843,748 A  * 12/1998  Nakada et al. .............. 435/193

FOREIGN PATENT DOCUMENTS

EP    0 841 397 A2    5/1998
JP    10-304881 A    11/1998

OTHER PUBLICATIONS

Bassily, Rafik, et al, "An improved synthesis of 4-azido-4-deoxy- and 4-amino-4-deoxy-α, α-trehalose and their epimers", Carbohydrate Research, vol. 239 (1993), pp. 197-207.
Gherna, Eds. "American Type Culture Collection: Catalogue of Bacteria and Phages"; 18$^{th}$ ed., 1992, Rockville, MD, pp. 452-456.
Lee, Cheang Kuan, "Synthesis of α-D-glucopyranosyl α-D-glactopyranoside", Carbohydrate Research, vol. 50 (1976), pp. 152-157.
Nakada, Tetsuya, et al, "Purification and Characterization of Trehalose from *Bacillus* sp. T3", Oyo Toshitsu Kagaku, vol. 42, No. 3, (1995), pp. 231-236.
Excerpt translation of "Standard Methods of Analysis in Food Safety Regulation", CHEMISTRY, (1991), pp. 21-22.

* cited by examiner

*Primary Examiner*—Keith Hendricks
*Assistant Examiner*—Jyoti Chawla
(74) *Attorney, Agent, or Firm*—Browdy and Neimark, PLLC

(57) ABSTRACT

A crystalline α-D-glucosyl α-D-galactoside which has a melting point of 119–123° C.; a saccharide composition comprising the same; a process for producing the same or the saccharide composition comprising the same, which comprises (i) crystallizing α-D-glucosyl α-D-galactoside from its solution and (ii) collecting the grown crystalline α-D-glucosyl α-D-galactoside; a method for converting amorphous α-D-glucosyl α-D-galactoside to crystalline α-D-glucosyl α-D-galactoside in the presence of moisture; and a composition comprising the crystalline α-D-glucosyl α-D-galactoside or the saccharide composition comprising the same.

13 Claims, 2 Drawing Sheets

CRYSTALLINE α-D-GLUCOSYL α-D-GALACTOSIDE, SACCHARIDE COMPOSITION COMPRISING THE SAME, PROCESS FOR PRODUCING THE SAME, AND USES THEREOF

BACKGROUND OF THE INVENTION

1. Field of the Invention

The present invention relates to a crystalline α-D-glucosyl α-D-galactoside which has a melting point of 119–123° C., a saccharide composition comprising the same, a process for producing the same, uses thereof, and a method to convert an amorphous α-D-glucosyl α-D-galactoside to a crystalline α-D-glucosyl α-D-galactoside.

2. Description of the Prior Art

Patent document No. 1: A Patent Kokai No. 304,881/98.

Non-patent document No. 1: "Carbohydrate Research", Vol. 50, pp. 152–157, 1976, by C. K. Lee et al.

Non-patent document No. 2: "Carbohydrate Research", Vol. 239, pp. 197–207, 1993, by R. W. Bassily et al.

An α-D-glucosyl α-D-galactoside is a non-reducing disaccharide, which glucose and galactose are linked each other via the α,α-1,1 linkage, and is an isomer of α,α-trehalose (hereinafter abbreviated as "trehalose"). Non-patent document Nos. 1 and 2 disclose an α-D-glucosyl α-D-galactoside which is organically synthesized, and the document No. 2 discloses its crystalline monohydrate with a melting point of 165–170° C. However, the above processes are complicated organic syntheses, their yields are relatively-low, it is difficult to produce them with a large quantity, and not only uses thereof but also an industrial production have not been developed at all. Thereafter, the same applicant as the present invention disclosed the synthesis of α-D-glucosyl α-D-galactoside by an enzymatic method using trehalose phosphorylase in the patent document No. 1 to enable to produce it with a large quantity.

α-D-Glucosyl α-D-galactoside has a fine sweetness; properties such as regulation of osmotic pressure, moisture absorption, gloss imparting ability, ability of preventing crystallization of other saccharides, and ability of preventing deterioration of starch; and functions such as cariostatic ability, ability of promoting growth of *bifidobacterium*, and ability of promoting absorption of minerals. Therefore, α-D-glucosyl α-D-galactoside has uses for many compositions such as food products, favorite foods, feed, baits, cosmetics, medicated cosmetics, pharmaceuticals, goods for life, products for agriculture, forestry and fisheries, reagents, and products for chemical industries. However, amorphous α-D-glucosyl α-D-galactoside had a problem of unstability, for example, the saccharide alone or a composition of other saccharide had a relatively-high moisture absorption and easily solidified, deliquesced, or lost fluidity. Therefore, it has not been easily applied in many fields in spite of its various usefulness.

SUMMARY OF THE INVENTION

The object of the present invention is to provide a stable crystalline α-D-glucosyl α-D-galactoside which has a relatively-low moisture absorption and substantially does not lose fluidity, a saccharide composition comprising the same, a process for producing the same, and uses thereof.

BRIEF DESCRIPTION OF THE ACCOMPANYING DRAWINGS

DETAILED DESCRIPTION OF THE INVENTION

Figure 1:
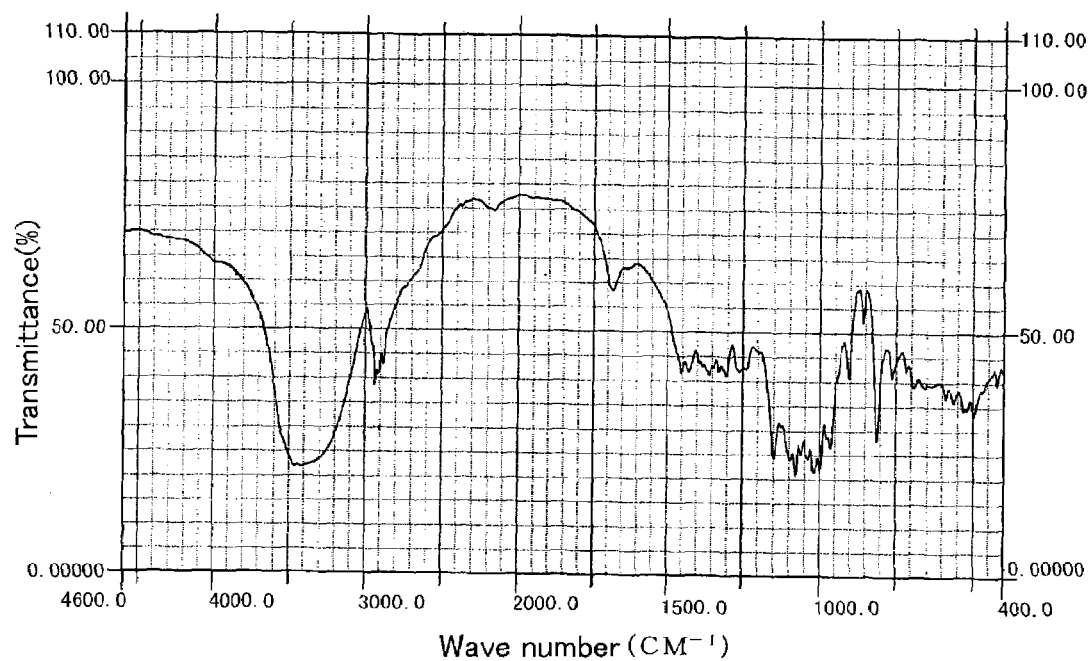
FIG. 1 is an infrared absorption spectrum of the crystalline α-D-glucosyl α-D-galactoside of the present invention.

The present inventors have eagerly studied to accomplish a stable α-D-glucosyl α-D-galactoside which has a relatively-low moisture absorption and substantially does not solidify, deliquesce, and lose fluidity. As a result, they obtained a crystalline α-D-glucosyl α-D-galactoside (hereinafter abbreviated as "crystalline α-D-glucosyl α-D-galactoside") by the enzymatic method disclosed by the patent document No. 1, examined the physiological properties, and unexpectedly found that a melting point of the crystalline was 119–123° C. and it differed from a crystalline disclosed in the non-patent document No. 2 by R. W. Bassily. The crystalline α-D-glucosyl α-D-galactoside is a novel crystalline obtainable by (i) crystallizing from a solution containing α-D-glucosyl α-D-galactoside or (ii) converting an amorphous α-D-glucosyl α-D-galactoside to its crystalline form in the presence of moisture. The crystalline has peaks at diffraction angles (2θ) of at least 13.4°, 17.4°, 19.7°, and 22.3° in X-ray powder diffraction analysis using a CuK α-ray as an X-ray. The crystalline has an endothermic peak in the range of about 118–138° C. on differential scanning calorimetry. Further, it is detected moisture of monohydrate as a bound water by the Karl Fischer method and has a spectrum in FIG. 1 when measured for infrared absorption spectrum by the potassium bromide tablet method.

In the process for producing the crystalline α-D-glucosyl α-D-galactoside of the present invention, origins of α-D-glucosyl α-D-galactoside as a material are not limited; it can be produced by an organic synthesis, fermentation method, enzymatic method, and method of extracting from natural materials such as organisms, animals and plants. The enzymatic method is generally preferable from safety and economical view points: For example, α-D-glucosyl α-D-galactoside disclosed in the patent document No. 1, which can be obtained by acting trehalose phosphorylase on β-D-glucose-monophosphate as a donor of glucosyl group and D-galactose as a recipient of glucosyl group, can be preferably used.

Though the present invention uses α-D-glucosyl α-D-galactoside as a material, it does not concern with a process for producing α-D-glucosyl α-D-galactoside. Therefore, the following outlines the process of the enzymatic method.

Any trehalose phosphorylase, which is used to produce α-D-glucosyl α-D-galactoside, can be used without limitation as long as having an ability of producing α-D-glucosyl α-D-galactoside. For example, the enzyme, disclosed in the patent document No. 1, from *Thermoanaerobium brockii* (ATCC 35047) from *Thermoanaerobium* strain has a relatively-high heat-resistance reacts at a relatively-high temperature, and has advantageous features of an efficient reaction and an avoidance of organism pollution. The above trehalose phosphorylase has the following physicochemical properties:

(1) Action
  (a) Resolving trehalose in the presence of an inorganic phosphoric acid to produce D-glucose and β-D-glucose-monophosphate;
  (b) Producing trehalose and an inorganic phosphoric acid from D-glucose and β-D-glucose-monophosphate, and further catalyzing the transfer of a glycosyl group to other saccharide by using β-D-glucose-monophosphate as a donor of a saccharide;
(2) Molecular weight Having a molecular weight of 88,000±5,000 daltons when determined on sodium dodecyl sulfate (SDS) polyacrylamide gel electrophoresis (PAGE)
(3) Isoelectric point (pI) Having a pI of 5.4±0.5 when determined on isoelectrophoresis using ampholine;
(4) Optimum temperature Having an optimum temperature of about 70° C. when incubated at pH 7.0 for 30 min;
(5) Optimum pH Having an optimum pH of around 7.0–7.5 when incubated at 60° C. for 30 min;
(6) Thermal stability Having a thermostable range at temperatures of around 60° C. when incubated at pH 7.0 for one hour;
(7) pH Stability Having a stable pH range at around pH 6.0–9.0 when incubated at 4° C. for 24 hours;
(8) Promoting an activity and stabilization Being promoted in the presence of one milimolar dithiothreitol; and
(9) Inhibition Being inhibited in the presence of one milimolar copper ion ($Cu^{++}$), lead ion ($Pb^{++}$), zinc ion ($Zn^{++}$), mercurous ion ($Hg^{++}$), magnesium ion ($Mg^{++}$), or manganese ion ($Mn^{++}$).

In an enzymatic reaction to produce α-D-glucosyl α-D-galactoside by using trehalose phosphorylase, α-D-glucosyl α-D-galactoside is usually produced by acting the enzyme on β-D-glucose monophosphate as a donor of glucosyl group and D-galactose as a recipient of glucosyl group, and transferring a glucosyl group to D-galactose. β-D-glucose monophosphate as a donor of glucosyl group can be used a product on the market and obtained by acting phosphorylase such as trehalose phosphorylase, maltose phosphorylase, sucrose phosphorylase, or cellobiose phosphorylase with saccharides as substrates in the presence of inorganic phosphoric acids and/or salts thereof. Productive yield of α-D-glucosyl α-D-galactoside depends on substrates used in their enzymatic reactions, substrate concentrations, and reaction conditions: For example, the productive yield is 30% (w/w) of a solid material, when used are 10% (w/w) of trehalose and five percents (w/w) of D-galactose as a substrate in the presence of an inorganic phosphoric acid.

Purity of α-D-glucosyl α-D-galactoside in the obtained reaction solutions can be increased by the D-glucose resolving method using microorganisms or enzymes to raise the content of α-D-glucosyl α-D-galactoside, yeast fermentative method to raise purity of the produced α-D-glucosyl α-D-galactoside, alkaline treatment method, membrane filtration method, and column chromatography method. Further, the reaction solutions can be concentrated and dried to obtain syrupy or powdery saccharides comprising α-D-glucosyl α-D-galactoside, after purification steps of such as filtration, decoloration, and desalting in a conventional manner, if necessary. The obtained saccharide compositions usually contain 5–99.9% (w/w) of α-D-glucosyl α-D-galactoside, on a dry solid basis (hereinafter abbreviated as "d.s.b").

The crystalline α-D-glucosyl α-D-galactoside of the present invention can be obtained by sequentially dissolving the aforesaid α-D-glucosyl α-D-galactoside in an appropriate solvent as undermentioned to obtain a supersaturated solution of α-D-glucosyl α-D-galactoside, and crystallizing the α-D-glucosyl α-D-galactoside from the supersaturated solution. In the case of conditions such as a purity and a solid concentration of α-D-glucosyl α-D-galactoside, solvents, and temperature are not particularly limited as long as the desired supersaturated solutions of α-D-glucosyl α-D-galactoside can be obtained. The form of a solution comprising α-D-glucosyl α-D-galactoside, which is used in the process for producing the crystalline α-D-glucosyl α-D-galactoside of the present invention, can be those which are suitable for producing the crystalline, for example, a solution or suspension form which has incompletely dissolved materials, and a deliquescent form which a powdery composition containing α-D-glucosyl α-D-galactoside absorbs moisture to deliquesce. As the solvents to dissolve α-D-glucosyl α-D-galactoside, water is usually preferable, and solvents which have compatibility to water such as methanol, ethanol, acetone, and pyridine, and aqueous solutions thereof are also arbitrarily used, if necessary. In the process for producing the crystalline α-D-glucosyl α-D-galactoside of the present invention, for example, solutions comprising α-D-glucosyl α-D-galactoside with a purity of at least 60% (w/w) and a solid concentration of 65–90% (w/w) are placed in a crystallizer, and cooled while mixing at 95° C. or lower, desirably in the range of 10–90° C., to obtain a massecuite comprising the crystalline α-D-glucosyl α-D-galactoside in the presence of 0.1–20% (w/w) of α-D-glucosyl α-D-galactoside as a seed crystal, if necessary. Continuative crystallization method to crystallize α-D-glucosyl α-D-galactoside while concentrating under a reduced pressure is advantageously applied. As the process for producing crystalline α-D-glucosyl α-D-galactoside or a molasses comprising the same from a massecuite, conventional methods can be applied, for example, separating method, block pulverizing method, fluidized granulating method, and spray-drying method.

In the separating method, crystalline α-D-glucosyl α-D-galactoside with a relatively-high purity can be produced by separating a massecuite into crystalline α-D-glucosyl α-D-galactoside and a molasses by a basket-type centrifuge, and further excluding impurities from the crystals by spraying thereto a small amount of cooled water, if necessary. In the spray-drying method, a massecuite with an α-D-glucosyl α-D-galactoside concentration of 70–85% (w/w) and a crystallization yield of 5–60% is, for example, sprayed through a rotatory disk or a nozzle by a high-pressure pump and dried by a hot air with a temperature of 60–100° C. which does not melt the crystalline powder, followed by aging for 1–48 hours with blowing a warm air with a temperature of 20–60° C. to facilitate the production of a relatively-low hygroscopic molasses. In the block pulverizing method, a massecuite with a moisture content of 5–20% (w/w) and a crystallization yield of 10–60% is left for about 0.1–7 days to solidify into a block form, and then the obtained block is pulverized by a crushing or scrapping method to easily produce a relatively-low hygroscopic molasses.

The process for producing the crystalline α-D-glucosyl α-D-galactoside of the present invention is to produce it from an amorphous α-D-glucosyl α-D-galactoside. In this process, a powder comprising an amorphous α-D-glucosyl α-D-galactoside is left or mixed for about 0.1–7 days to change it to crystalline α-D-glucosyl α-D-galactoside under a condition controlled at about 20–60° C. in the presence of moisture, and the obtained crystal is repulverized by crushing or scrapping to easily produce crystalline α-D-glucosyl α-D-galactoside with a relatively-low hygroscopicity or a saccharide composition comprising the same. In this process, "in the presence of moisture" is not specifically limited as far as moisture to convert an amorphous α-D-glucosyl α-D-galactoside into crystalline α-D-glucosyl α-D-galactoside is supplied, and it usually means a condition controlled at a relative humidity of about 50–70%.

The crystalline α-D-glucosyl α-D-galactoside and the saccharide composition comprising the same according to the present invention usually comprise the crystalline in an amount of 50% (w/w) or higher, and desirably, 60–99.99% (w/w).

The crystalline α-D-glucosyl α-D-galactoside and the saccharide composition of the same of the present invention are easily handlable and stable, have a remarkably-low hygroscopicity in a solid or powdery form, have fine sweetness and properties such as regulation of osmotic pressure, moisture absorption, gloss imparting ability, ability of preventing crystallization of other saccharides, and ability of preventing deterioration of starch; and further have functions such cariostatic ability, ability of promoting growth of *bifidobacterium*, and ability of promoting absorption of minerals. Therefore, they can be utilized in compositions such as food products, favorite foods, feeds, baits, cosmetics, medicated cosmetics, pharmaceuticals, goods of life, reagents, products of chemical industries, and products of agriculture, forestry and fisheries.

The crystalline α-D-glucosyl α-D-galactoside and the saccharide composition comprising the same of the present invention can be used as seasonings to give sweetness. If necessary, they can be utilized by mixing together with one or more other sweeteners such as starch syrup powder, glucose, maltose, trehalose, sucrose, isomerized saccharide, honey, maple sugar, sorbitol, maltitol, lactitol, dihydrochalcones, stevioside, α-glycosylstevioside, rebaudioside, glycyrrhizin, L-aspartylphenylalanine methylester, sucralose, acesulfam K, saccharin, glycine, and alanine at an appropriate ratio. Further, they can be utilized by mixing with one or more appropriate fillers such as dextrin, starch, and lactose.

The taste of the crystalline α-D-glucosyl α-D-galactoside and the saccharide composition comprising the same of the present invention well harmonize with other materials having a sour-, acid-, salty-, astringent-, delicious-, or bitter-taste; and have a satisfactorily-high acid- or heat-tolerance. Thus, they can be favorably used to sweeten and/or improve the taste and the quality of food products in general, for example, a soy sauce, powdered soy sauce, miso, "funmatsu-miso" (a powdered miso), "moromi" (a refined sake), "hishio" (a refined soy sauce), "furikake" (a seasoned fish meal), mayonnaise, dressing, vinegar, "sanbai-zu" (a sauce of sugar, soy sauce and vinegar), "funmatsu-sushi-su" (powdered vinegar for sushi), "chuka-no-moto" (an instant mix for Chinese dish), "tentsuyu" (a sauce for Japanese deep-fat fried food), "mentsuyu" (a sauce for Japanese vermicelli), sauce, catsup, "takuan-zuke-no-moto" (a premix for pickled radish), "hakusai-zuke-no-moto" (a premix for fresh white rape pickles), "yakiniku-no-tare" (a sauce for Japanese grilled meat), curry roux, instant stew mix, instant soup mix, "dashi-no-moto" (an instant stock mix), mixed seasoning, "mirin" (a sweet sake), "shin-mirin" (a synthetic mirin), table sugar, and coffee sugar.

The crystalline α-D-glucosyl α-D-galactoside and the saccharide composition comprising the same of the present invention can be advantageously utilized to sweeten and improve the taste and the quality of "wagashi" (Japanese cakes) such as "senbei" (a rice cracker), "arare" (a rice cake cube), "okoshi" (a millet-and-rice cake) "mochi" (a rice paste) and the like, "manju" (a bun with a bean-jam), "uiro" (a sweet rice jelly), "an" (a bean jam) and the like, "yokan" (a sweet jelly of beans), "mizu-yokan" (a soft adzuki-bean jelly), "kingyoku" (a kind of yokan), jelly, pao de Castella, and "amedama" (a Japanese toffee); Western confectioneries such as a bread, biscuit, cracker, cookie, pie, pudding, butter cream, custard cream, cream puff, waffle, sponge cake, doughnut, chocolate, chewing gum, caramel, and candy; frozen desserts such as an ice cream and sherbet; syrups such as a "kajitsu-no-syrup-zuke" (a preserved fruit) and "korimitsu" (a sugar syrup for shaved ice); pastes such as a flour paste, peanut paste, fruit paste, and spread; processed fruits and vegetables such as a jam, marmalade, "syrup-zuke" (fruit pickles), and "toka" (conserves); pickles and pickled products such as a "fukusin-zuke" (red colored radish pickles), "bettara-zuke" (a kind of whole fresh radish pickles), "senmai-zuke" (a kind of sliced fresh radish pickles), and "rakkyo-zuke" (pickled shallots); meat products such as a ham and sausage; products of fish meat such as a fish ham, fish sausage, "kamaboko" (a steamed fish paste), "chikuwa" (a kind of fish paste), and "tenpura" (a Japanese deep-fat fried fish paste); "chinmi" (relish) such as a "uni-no-shiokara" (salted guts of sea urchin), "ika-no-shiokara" (salted guts of squid), "su-konbu" (processed tangle), "saki-surume" (dried squid strips), "fugu-no-mirin-boshi" (a dried mirin-seasoned swellfish); "tsukudani" (foods boiled down in soy sauce) such as those of laver, edible wild plants, dried squid, small fish, and shellfish; daily dishes such as a "nimame" (cooked beans), potato salad, and "konbu-maki" (a tangle roll); milk products; canned and bottled products such as those of meat, fish meat, fruit, and vegetable; alcoholic beverages such as a sake, synthetic sake, liqueur, and foreign liquor; soft drinks such as a tea, coffee, cocoa, juice, carbonated beverage, sour milk beverage, and beverage containing a lactic acid bacterium; instant food products such as instant pudding mix, instant hot cake mix, "sokuseki-shiruko" (an instant mix of adzuki-bean soup with rice cake), and instant soup mix; and other foods and beverages such as solid foods for babies, foods for therapy, health/tonic drinks, rice, noodles, and frozen foods.

Since the crystalline α-D-glucosyl α-D-galactoside and the saccharide composition comprising the same of the present invention has a superior moisture-retaining ability, they can be also advantageously utilized as a material of cosmetics and medicated cosmetics in any forms such as a solution, soluble, emulsion, powder dispersion, double layers of water and oil, double layers of water and powder, and triple layers of water, oil, and powder. These cosmetics and medicated cosmetics have many uses, for example, basic skin cares, cleansing cosmetics, lotions, creams, milky lotions, packs, foundations, face powders, pressed powders, lipsticks and rouge, eye make up cosmetics, cheek colors, perfumes, bath cosmetics, bath preparations, oral health care agents, suntan and sunscreen cosmetics, make up cosmetics, facial cosmetics, oils and fats for cosmetics, fragrance cosmetics, body care cosmetics, hair care cosmetics, hair cleansing cosmetics, soap, medicated soap, detergents, dentifrices, mouth fresheners, deodorant cosmetics, bath dusting powder, hair growth promoters, shaving cosmetics, and preventing and therapeutic medicaments for many diseases such as inflammation, infection disease, allergy, atopy, ulcer, and tumor in a lotion, milky lotion, cream, ointment, kneaded agent, suspending agent, emulsifier, paste, stick, solid, semisolid, powdery, shaped powdery, jelly, gel, aerosol, troche, pack, or facemask form. Their concrete examples are a face cleansing cream, face cleansing foam, cleansing cream, cleansing milky lotion, cleansing oil, massage cream, cold cream, moisture cream, moisture lotion, milky lotion, lotion, liquid foundation, powdery foundation, lipstick, lip cream, pack, after shaving cream, after shaving lotion, sunscreen cream, suntan oil, body shampoo, hair shampoo, hair rinse, hair treatment, tonic, hair growth promoter, hair stick, hair cream, hair liquid, setting lotion, hair spray, hair mousse, hair dye, hair bleach, color rinse, color spray, permanent wave lotion, pressed powder, loose powder, eye shadow, hand cream, depilatory cream, eau de cologne, deodorant bath preparation, bath oil, oral deodorant, oral fragrance product, gargle, mouthwash, dental paste, ointment for curing an external wound, antibacterial cream, steroid ointment, and detergent.

Since the crystalline α-D-glucosyl α-D-galactoside and the saccharide composition comprising the same of the present invention are stable, they can be used at any ratio and/or in any combination with one or more materials selected from the group consisting of saccharides, materials with a blood-circulation promoting effect, materials with an antiinflammatory effect, materials with an antibacterial effect, materials with a moisture-retaining effect, materials with a whitening effect, materials with an antioxidative effect, kankoso, materials with an UV absorbing effect, materials with an UV scattering effect, and materials with an emulsifying effect. If necessary, one or more materials selected from the group consisting of the following materials can be appropriately used; (i) ingredients printed in "Japanese Standards of Cosmetic Ingredients", "Supplement To The Japanese Cosmetic Ingredients Codex", "The Comprehensive Cosmetic Ingredients Codex", "The Medicated Cosmetics Ingredients Codex", "The Pharmacopoeia of Japan", "Supplement To The Pharmacopoeia of Japan Codex", "The Pharmaceutical Additives Codex", "Supplemental Crude Drug To The Pharmacopoeia of Japan Codex", and "Food Additives Codex"; (ii) ingredients with the aforesaid effects disclosed in "New Cosmetic Science, a Second Revised and Enlarged Edition", published by Yakuji Nippo Ltd. on Jul. 10, 1992 and "New Cosmetology", published by NAN-ZANDO Co., Ltd. on Jan. 18, 1992; and (iii) materials other than the above ingredients which are used in conventional pharmaceuticals, medicated cosmetics, and cosmetics such as a pharmaceutical, excipient, base, emollient agent, cool-feeling agent, astringent, dispersant, solubilizer, solvent, alkaline chemical, viscosity controlling agent, thickener, foaming agent, antifoaming agent, aromatizing agent, coloring agent, stabilizer, antiseptic agent, fungicide, decoloring preventing agent, hair treating agent, humectant, hair protecting agent, antistatic preventing agent, auxiliaries, resolvent, dissolving coadjuvant, fluidization, suspending agent, buffer, sweetener, refrigerant agent, flavoring agent, binder, absorption agent, spraying agent, coating agent, masticatory agent, packing agent, softener, adjuster, metal sealing agent, discoloration preventing agent, oil and fat, oil soluble polymer, inorganic and organic pigments, inorganic and organic pigments treated with silicone or fluorine compound, color reagents such as organic dye, photosensitizing dye such as "Lumin™", wax, antiperspirant, deodorant, anti-wrinkle agent, sebum secretion inhibitor, anti-seborrhea agent, corneocyte desquamating agent, painkiller, and anti-plasmin agent.

Further, the crystalline α-D-glucosyl α-D-galactoside and the saccharide composition comprising the same of the present invention can be advantageously utilized to improve the taste of feeds and baits for breeding animals such as domestic animals, fouls, and fishes. They can be arbitrary used in a solid, paste or liquid form as a sweetener, taste improving agent, taste preference-improving agent, and quality improving agent for pharmaceuticals and preferences such as tobaccos, cigarettes, tooth pastes, lipsticks, rouges, lip creams, internal liquid medicines, tablets, troches, cod liver oil in the form of drop, oral refrigerants, oral fragrances, and gargles.

As α-D-glucosyl α-D-galactoside has an α-D-galactosyl group, it is expected to suppress cancer cells, activate natural-killer (NK) cells, improve atopic dermatitis, activate immunity, neutralize verotoxin of O157, a pathological *E. coli*, treat hepatic encephalopathy, stabilize bull's semen in a freezing storage, and stabilize organs for grafting in transporting; and be used in these fields similarly as galactobiose, melibiose, or raffinose with an α-D-galactosyl group. Thus, crystalline α-D-glucosyl α-D-galactoside and the saccharide composition comprising the same of the present invention can be advantageously used for the above objects.

The crystalline α-D-glucosyl α-D-galactoside and the saccharide composition comprising the same of the present invention can be advantageously applied to many biologically active substances, which are susceptible to lose activities of their effective ingredients, health foods, cosmetics, medicated cosmetics, and pharmaceuticals containing them as a quality-improving agent or stabilizer. The crystalline α-D-glucosyl α-D-galactoside and the saccharide composition comprising the same of the present invention can be added to the following biologically active substances in an appropriate amount to easily produce stable health foods, cosmetics, medicated cosmetics, and pharmaceuticals free from losing activities of their effective ingredients, for example, liquid preparations containing lymphokines such as α-, β- and γ-interferons, tumor necrosis factor-α (TNF-α), tumor necrosis factor-β (TNF-β), macrophage migration inhibitory factor, colony-stimulating factor, transfer factor, and interleukin-1, interleukin-2, interleukin-6, interleukin-12, and interleukin-15; liquid preparations containing hormones such as insulin, growth hormone, prolactin, erythropoietin, tissue-type plasminogen activator, follicle-stimulating hormone, and placentral hormone; biological preparations such as BCG vaccine, Japanese encephalitis vaccine, measles vaccine, live polio vaccine, smallpox vaccine, tetanus toxoid, Trimeresurus antitoxin, and human immunoglobulin; antibiotics such as penicillin, erythromycin, chloramphenicol, tetracycline, streptomycin, and kanamycin sulfate; liquid preparations containing vitamins such as thiamine, riboflavin, L-ascorbic acid, cod liver oil, carotenoid, ergosterol, and tocopherol; solutions of enzymes such as lipase, elastase, urokinase, protease, β-amylase, isoamylase, glucanase, and lactase; extracts such as ginseng extract, snapping turtle extract, chlorella extract, aloe extract, and propolis extract; viable cells such as virus, acidophilus, and yeast; and royal jelly.

These compositions of the present invention include oral- or non-oral-compositions such as food products, cosmetics, medicated cosmetics, pharmaceuticals, goods for life, reagents, and products for chemical industries, and products for agriculture, forestry and fisheries.

The crystalline α-D-glucosyl α-D-galactoside and the saccharide composition comprising the same of the present invention can be incorporating into the above compositions before completion of their processings, and which can be appropriately selected from among the following conventional methods; mixing, dissolving, soaking, penetrating, sprinkling, coating, spraying, injecting, and solidifying. The amount of the crystalline α-D-glucosyl α-D-galactoside to be incorporated into the above compositions is usually in an amount of at least 0.01%, desirably, at least 0.1% (w/w), and more desirably, 1–99.99% (w/w) as a percentage of the solid weight to a total weight.

The following experiments explain the present invention in detail:

Experiment 1

Production of Trehalose Phosphorylase

A culture medium was prepared according to the preparation procedure of *Thermoanaerobacter brockii* medium in "ATCC catalogue of Bacteria and Bacteriophages, 18$^{th}$ Edition" pp. 452–456, published by American Type Culture Collection, 1992, except for replacing 0.5% (w/v) glucose with 0.5% (w/v) trehalose as a carbon source. Aliquots of 100 ml were placed in 100-ml pressure bottles, and seeded with *Thermoanaerobacter brockii*, ATCC 35047, followed by culturing at 60° C. for 48 hours for a seed culture.

About 10 L of a fresh preparation of the same culture medium as used in the above seed culture were placed in four 11-L stainless-steel bottles, sterilized by heating, and then cooled to 60° C. and inoculated with one percent (v/v) of the seed culture, followed by culturing at 60° C. for about 40 hours.

About 40 L of the resulting total cultures were centrifuged to obtain 92 grams (g) of cells. The cells were suspended in 10 mM phosphate buffer, ultrasonically crushed, and centrifuged to obtain a culture supernatant having the trehalose phosphorylase activity of 0.3 unit/ml. The supernatant was concentrated with a UF membrane to obtain an about 360 ml of enzyme concentrate having an activity of about 30 units/ml of trehalose phosphorylase.

The activity of trehalose phosphorylase was assayed as follows:
(1) Add a 0.2 ml of an enzyme solution to two milliliters of 20 mM phosphate buffer (pH 7.0) including 1.0% (w/v) trehalose as a substrate, react the mixture solution at 60° C. for 30 min, and stop the enzymatic reaction by boiling a sampled 0.5 ml of the reaction mixture at 100° C. for 10 min;
(2) admix 0.5 ml of a D-glucose oxidase/peroxidase reagent to the reaction mixture, allow to stand at 40° C. for 30 min, add 2.5 ml of 5 N hydrochloric acid to the mixture, and measure the absorbance at a wavelength of 525 nm; and
(3) define one unit activity of trehalose phosphorylase as the enzyme amount that forms one micromole of D-glucose per minute under the above enzymatic reaction conditions.

Experiment 2

Purification of Trehalose Phosphorylase

Three hundred milliliters of the enzyme concentrate obtained in Experiment 1 was dialyzed against 10 mM phosphate buffer (pH 7.0) for 24 hours and centrifuged to remove insolubles. Three hundred and eighty milliliters (380 ml) of the obtained supernatant was subjected to an ion-exchange chromatography using 380 ml of "DEAE-TOYOPEARL 650" gel, commercialized by Tosoh Corporation, Tokyo, Japan.

Trehalose phosphorylase was absorbed to "DEAE-TOYOPEARL 650" gel and eluted from the column with a linear gradient increasing from 0 M to 0.5 M of sodium chloride (a saline solution). Fractions, which were eluted at about 0.1 M of sodium chloride, were collected and further purified by the following method. The fractions were pooled and dialyzed against 10 mM phosphate buffer (pH 7.0) containing 1.5 M ammonium sulfate, and the dialyzed solution was centrifuged to remove insolubles, followed by subjecting to a hydrophobic column chromatography using 100 ml of "BUTYL-TOYOPEARL 650", a gel commercialized by Tosoh Corporation, Tokyo, Japan. In eluting with a linear gradient decreasing from 1.5 M to 0.5 M of ammonium sulfate, trehalose phosphorylase was eluted and collected as fractions with the enzyme activity. Further, the fractions were pooled and subjected to a gel filtration chromatography using 300 ml of "Ultrogel® AcA44", a gel commercialized by Sepracor Co., France, to collect fractions with the enzyme activity.

The purified enzyme specimen had a yield of about 25% for the aforesaid culture supernatant in terms of the activity of trehalose phosphorylase, and a specific activity of the purified enzyme sample was 78.2 units/mg protein.

The purified enzyme was subjected to a gel electrophoresis containing 7.5% (w/v) polyacrylamide to examine purity. The result showed that it was a relatively-high purified enzyme with an only one band.

Experiment 3

Preparation of α-D-glucosyl α-D-galactoside

Figure 2:
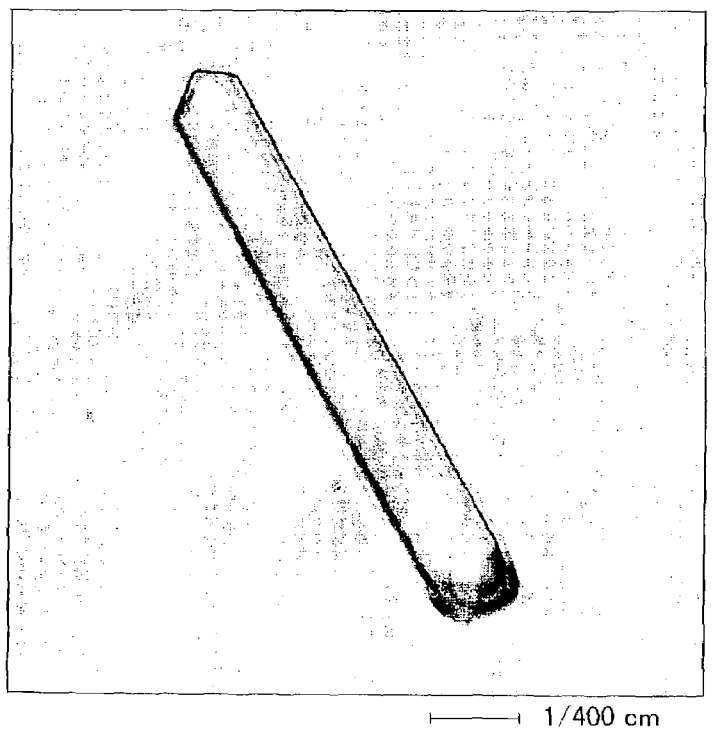
FIG. 2 is an intermediate tone view of a microscopic photograph of the crystalline α-D-glucosyl α-D-galactoside of the present invention in a pillar form.

A solution containing 4.5% (w/w) of trehalose, 2.5% (w/w) of D-galactose, and 5 mM sodium phosphate dihydrate was adjusted to pH 5.0, and admixed with 17 units of the purified trehalose phosphorylase in Experiment 2 per gram of trehalose, followed by enzymatically reacting at 60° C. for 96 hours. The reaction mixture was heated at 90° C. for 30 min to inactivate the enzyme and cooled. To examine purity of α-D-glucosyl α-D-galactoside in the mixture, a portion sample from the reaction mixture was dried, dissolved in pyridine, trimethylsilylated, and subjected to gas chromatography (hereinafter abbreviated as "GC"). The apparatus and conditions used in the GC analysis were a stainless-steel column, 3 mm in diameter and 2 m in length, packed with two percents of "SILICONE OV-17/CHROMOSORB W" commercialized by GL Science Inc., Tokyo, Japan; a flow rate of 40 ml/min of nitrogen gas as a carrier gas; and a ratio of increasing temperature in an oven, 7.5° C./min ranging from 160° C. to 320° C. The above reaction mixture was analyzed on a hydrogen flame ionization detector, founding that it comprised about 30% (w/w) of α-D-glucosyl α-D-galactoside based, d.s.b. To assimilate D-glucose in the reaction mixture, a commercialized baker's yeast was added in an amount of 30% by wet weight, d.s.b, and incubated at 27° C. for six hours while controlling to pH 5–6 with 1 M sodium hydroxide. The obtained mixture was centrifuged to remove the baker's yeast, and the obtained supernatant was adjusted to pH 7.5 with 1 M sodium hydroxide, admixed with 10 units of trehalase from *Bacillus* sp. T3, which had been prepared according to the method in "Journal of Applied Glycoscience", Vol. 42, pp. 231–236, 1995, per gram of solids, and incubated at 45° C. for 24 hours to hydrolyze trehalose to D-glucose. The obtained reaction mixture was heated at about 100° C., gradually admixed with a small amount of grained sodium hydroxide, and then kept at 100° C. and at a pH of 10–11 for one hour to decompose a reducing saccharide such as D-glucose. The obtained solution was neutralized with hydrochloric acid, decolored in a conventional manner with an activated carbon, filtrated, desalted and purified by H- and OH-type ion exchange resins, and further concentrated to obtain a syrup with a solid concentration of about 80% (w/w) in a yield of about 25%, d.s.b. GC analysis found that the syrup comprised 88.1% (w/w) of α-D-glucosyl α-D-galactoside, 7.5% (w/w) of glycerol, 1.0% (w/w) of trehalose, and 3.4% (w/w) of other saccharides. The syrup was spread over a glass plate, which was then placed in an incubator and left at 40° C. for two days under a normal pressure to produce a crystallized material in a pillar form as shown in FIG. 2. All the samples including the crystallized material were placed in a glass mortar, admixed with 100 ml of 85% (v/v) aqueous ethanol solution to wash the material while crushing. The resulting crystallized material was transferred to a glass filter and filtrated while aspirating air. Further, the obtained crystallized material was washed with 100 ml of 85% (v/v) aqueous ethanol solution and filtrated while aspirating air. The crystallized material on the filter was collected and dried at 40° C. for 16 hours in vacuo to obtain a crystalline powder in a yield of about 17%, d.s.b. GC analysis found that the obtained crystalline powder consisted of 98.4% (w/w) of α-D-glucosyl α-D-galactoside, d.s.b.

Experiment 4

Analysis by Powdery X-Ray Diffraction Analysis

Figure 3:
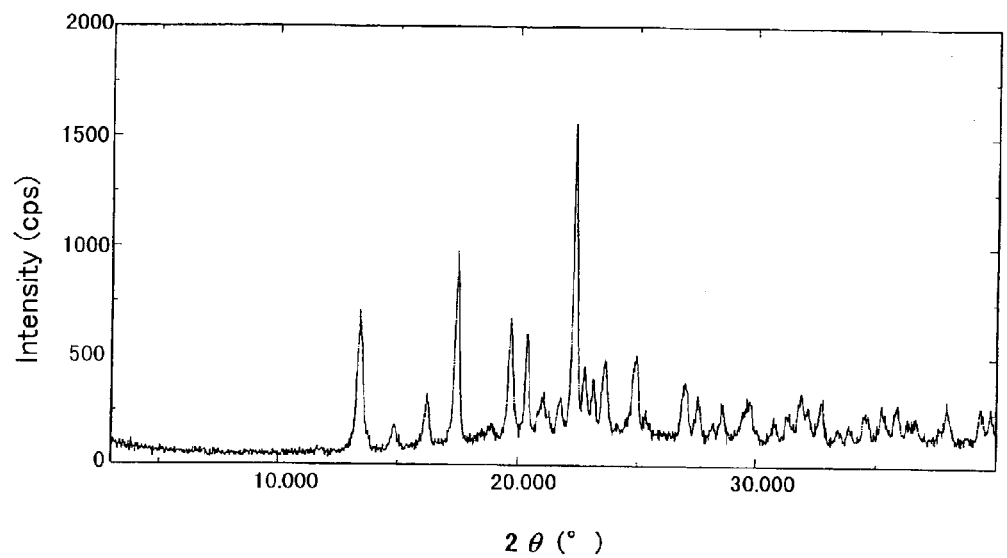
FIG. 3 is an powdery X-ray differential spectrum of the crystalline α-D-glucosyl α-D-galactoside of the present invention.

The crystalline powder of α-D-glucosyl α-D-galactoside obtained in Experiment 3 was examined for crystallinity by powdery X-ray diffraction analysis by using "GEIGER-FLEX RAD-IIB™", an X-ray diffraction analyzer using Cuk α ray commercialized by Rigaku Corporation, Tokyo, Japan, to obtain a spectrum as shown in FIG. 3 having peaks with diffraction angles (2θ) of at least 13.4°, 17.4°, 19.7°, and 22.3°. Crystallinity of the crystallized powder was calculated to be about 72.5% by using "Program for Crystallinity Analysis by Ruland method", a computer program installed in the analyzer. These results found that the powder was crystalline α-D-glucosyl α-D-galactoside having peaks with diffraction angles (2θ) of at least 13.4°, 17.4°, 19.7°, and 22.3° on a powdery X-ray diffraction analysis using Cuk α ray as X-ray.

Experiment 5

Measurement of Moisture

The crystalline powder of α-D-glucosyl α-D-galactoside obtained in Experiment 3 was examined for moisture by the Karl Fischer method, revealing that it had a moisture content of 5.4% (w/w). Since the theoretical moisture level of crystalline α-D-glucosyl α-D-galactoside monohydrate was five percents (w/w), it was concluded that the α-D-glucosyl α-D-galactoside obtained in Experiment 3 was in the form of a monohydrate.

Experiment 6

Measurement of Melting Point

The crystalline powder of α-D-glucosyl α-D-galactoside obtained in Experiment 3 was examined for melting point by using "MP-21 type™", a melting point measuring machine commercialized by Yamato Scientific Co., Ltd., Tokyo, Japan, founding that the melting point was 119–123° C. Since the melting point was completely different from a melting point of 165–170° C. for a crystalline α-D-glucosyl α-D-galactoside disclosed in the non-patent document No. 2, it was concluded that both crystals obtained in Experiment 3 and disclosed in the non-patent document No. 2 were completely different.

Experiment 7

Measurement of Infrared Spectrophotometry

The crystallized powder of α-D-glucosyl α-D-galactoside obtained in Experiment 3 was subjected to a potassium bromide tablet method by using "FTIR-8200™", an infrared spectrometer commercialized by Shimadzu Corporation, Tokyo, Japan, to obtain an infrared spectrum as shown in FIG. 1.

Experiment 8

Analysis on Differential Scanning Calorimeter (DSC)

Figure 4:
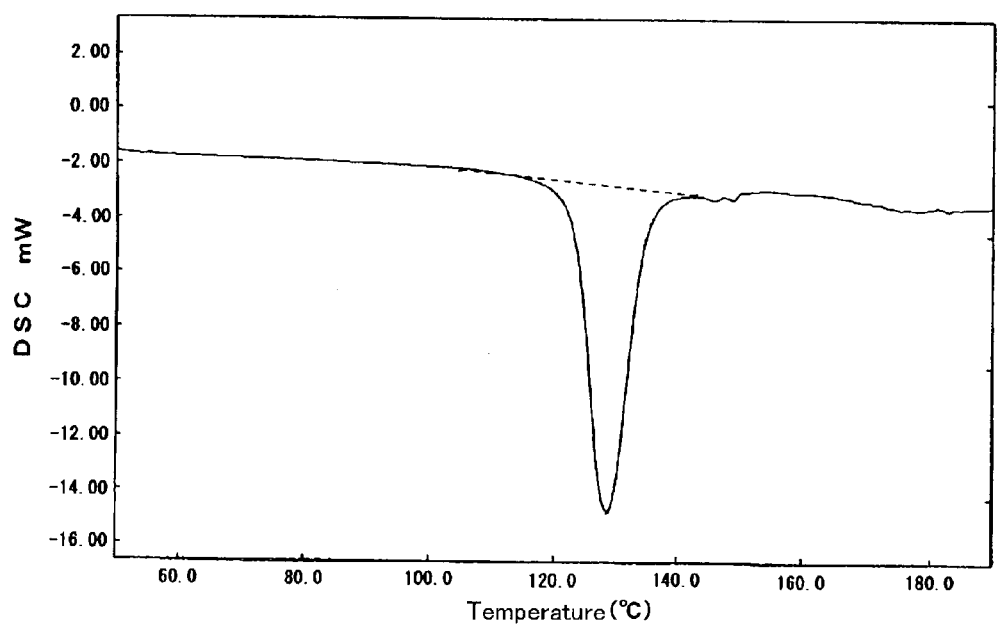
FIG. 4 is a differential scanning calorimetry chart of the crystalline α-D-glucosyl α-D-galactoside of the present invention.

4.4 milligrams of the crystalline powder of α-D-glucosyl α-D-galactoside obtained in Experiment 3 was placed in an aluminum vessel sealed, and then subjected to a differential scanning calorimetry by using "DSC 2200™", a differential scanning calorimeter commercialized by Seiko Instruments Inc., Chiba, Japan. The differential scanning calorimetry was performed by a temperature program using a ratio of increasing temperature of 10° C./min ranging from 30° C. to 200° C. to obtain a result as shown in FIG. 4. The result showed that the crystalline powder had an endothermic peak in the range of about 118–138° C.

Experiment 9

Saturated Concentration for Water

A surplus volume of the crystalline powder of α-D-glucosyl α-D-galactoside obtained in Experiment 3 was added to 10 ml of distilled water, shaken at 25° C. or 40° C. for 48 hours, and filtrated to collect a crystalline powder, which is more than the solubility, by using a 0.45 μm filter, followed by collecting two filtrates (saturated solutions). Moisture content of the filtrates was measured by using a desiccating agent method described in "Standard Methods of Analysis in Food Safety Regulation, Chemistry" published by Japan Food Hygiene Association under the editorship of Ministry of Health, Labor and Welfare, 1991, to examine a saturated concentration of α-D-glucosyl α-D-galactoside. As a result, it was found that α-D-glucosyl α-D-galactoside had saturated concentrations in water of 68.9% (w/w) at 25° C., and 71.8% (w/w) at 40° C., d.s.b.

Experiment 10

Moisture Absorption Test on Crystalline α-D-glucosyl α-D-galactoside

A half gram aliquots of the crystalline powder of α-D-glucosyl α-D-galactoside obtained in Experiment 3 were placed in aluminum weighing cans, which had been precisely weighed in advance, and each weighing can was weighed. The weight of each weighing can was subtracted from the total weight to calculate the starting weight of the crystalline powder of α-D-glucosyl α-D-galactoside. Each weighing can with the crystalline powder of α-D-glucosyl α-D-galactoside was placed in a glass desiccator which the relative humidity was controlled to a level of 33–99% in advance, and stored at 25° C. for one to seven days while keeping at the desired humidity. After the moisture absorption test, each weighing can had been precisely weighted and calculated for increasing weight to obtain a moisture absorption level (%). In the test, the crystalline powder was macroscopically observed. These results are in Table 1.

TABLE 1

| Relative humidity | Storage | | | | | | | |
|---|---|---|---|---|---|---|---|---|
| | One day | | Two days | | Three days | | Seven days | |
| (%) | A(%) | Appearance | A(%) | Appearance | A(%) | Appearance | A(%) | Appearance |
| 90 | 6.9 | p.d. | 11.8 | p.d. | 19.2 | Deliquescence | 42.1 | Deliquescence |
| 84 | 3.2 | Hardened | 4.4 | Hardened | 6.1 | Hardened | 11.0 | Hardened |
| 75 | 0.1 | Unchanged | 0.1 | Unchanged | 0.1 | Unchanged | 0.2 | Unchanged |
| 60 | 0.1 | Unchanged | 0.1 | Unchanged | 0.1 | Unchanged | 0.2 | Unchanged |
| 53 | 0.0 | Unchanged | 0.0 | Unchanged | 0.0 | Unchanged | 0.1 | Unchanged |
| 43 | 0.0 | Unchanged | 0.0 | Unchanged | 0.0 | Unchanged | 0.0 | Unchanged |
| 33 | 0.0 | Unchanged | 0.0 | Unchanged | 0.0 | Unchanged | 0.0 | Unchanged |

Note
A(%)*: Moisture absorption level
p.d.: Partial deliquescence

As shown in Table 1, crystalline α-D-glucosyl α-D-galactoside absorbed moisture under relative humidities of 90% and 84% to deliquesced or hardened, and it did not absorb moisture in a relative humidity of 75% or lower and the appearance was not changed. Compared these results with the results of the amorphous powder of α-D-glucosyl α-D-galactoside in Table 2 of the following Experiment 11, it was found that the crystalline power substantially does not absorb moisture and stable compared with the amorphous powder.

Experiment 11

Moisture Absorption Test on Amorphous α-D-glucosyl α-D-galactoside

The crystalline powder of α-D-glucosyl α-D-galactoside obtained in Experiment 3 was dissolved in water to obtain an aqueous solution with a concentration of 30% (w/w). The resultant aqueous solution was frozen and dried into an amorphous powder of α-D-glucosyl α-D-galactoside. Similar as in Experiment 10, the obtained amorphous powder was placed in aluminum weighing cans, and the cans were placed in a glass desiccator which the relative humidity was controlled to a level of 43–90% in advance, and stored at 25° C. for one to seven days while keeping at the desired humidity. After the moisture absorption test, moisture absorption level (%) was calculated similarly as in Experiment 10. In the test, the appearance of each powder was macroscopically observed. Samples after a storage for seven days were confirmed for their appearance by a powdery X-ray diffraction analysis in Experiment 4, and samples with crystals were examined for their crystallinity. These results are in Table 2.

As shown in Table 2, it was found that the amorphous powder of α-D-glucosyl α-D-galactoside remarkably absorbed moisture under a relative humidity of 43–90%, hardened, wetted, solidified, and deliquesced; and the appearance remarkably changed with the passage of time. In detail, the powdery surface became wet when storaged for one day, and the powder totally hardened under relative humidities of 60% and 53% after a storage for seven days. Analysis of hardened samples found that the amorphous powder of α-D-glucosyl α-D-galactoside changed to α-D-glucosyl α-D-galactoside, monohydrate. α-D-glucosyl α-D-galactoside monohydrate had a melting point of 119–123° C. Under a relative humidity of 43%, the amorphous powder of α-D-glucosyl α-D-galactoside kept an amorphous condition, though it absorbed moisture and solidified as a whole. Since the crystalline of α-D-glucosyl α-D-galactoside observed in this Experiment absorbed moisture to convert to a crystal and the pattern by a powdery X-ray diffraction analysis agreed with that of α-D-glucosyl α-D-galactoside monohydrate measured in Experiment 4, it was concluded that the crystal had a monohydrate.

The above results showed that a crystalline powder of α-D-glucosyl α-D-galactoside dose not substantially absorb moisture, and is stable and easily handlable under a condition of a relative humidity of 75% or lower. It was revealed that the crystalline powder has a satisfactory moisture absorption-resistance to conventional amorphous powders of α-D-glucosyl α-D-galactoside.

The following Example A explains the process for producing the crystalline α-D-glucosyl α-D-galactoside of the present invention.

TABLE 2

| Relative humidity | Storage for one day | | Storage for seven days | | | |
|---|---|---|---|---|---|---|
| (%) | A(%)* | Appearance | A(%)* | Appearance | Diffraction spectrum | Crystallinity |
| 90 | 13.2 | Partial deliquescence | 36.2 | Deliquescence | — | — |
| 60 | 3.1 | Wet on the surface | 2.0 | Hardened | Crystal monohydrate | 71 |
| 53 | 3.5 | Wet on the surface | 1.8 | Hardened | Crystal monohydrate | 67 |
| 43 | 4.5 | Solidified | 6.3 | Solidified | Amorphous | — |

Note
A(%)*: Moisture absorption level
Appearance is macroscopically observed.

EXAMPLE A-1

A Powdery Crystalline α-D-glucosyl α-D-galactoside

A solution containing 5.0% (w/w) of trehalose, 2.5% (w/w) of D-galactose, and 5 mM sodium phosphate dihydrate was adjusted to pH 5.0, and admixed with 15 units/g trehalose of a purified trehalose phosphorylase prepared by the method in Experiment 1 per gram of trehalose, followed by reacting at 60° C. for 72 hours. The reaction mixture was heated at 95° C. for 30 min to inactivate the enzyme, cooled down to 45° C., adjusted to pH 7.5, admixed with 10 units/g solids of trehalase from *Bacillus* sp. T3, produced by Hayashibara Biochemical Laboratories, Inc., Okayama, Japan, and incubated at 45° C. for 24 hours. The obtained reaction mixture was heated at 90° C. for 30 min to inactivate the enzyme, admixed with a commercialized baker's yeast in an amount of five percents of a wet weight to the solids, incubated at 27° C. for six hours, while controlling the pH to 5–6 by using 1 M sodium hydroxide to assimilate D-glucose. The resulting mixture was centrifuged to remove the cells, and the obtained supernatant was in a conventional manner decolored with an activated carbon, filtrated, desalted, and purified by ion exchange resins in H- and OH-forms, and further concentrated into an about 45% (w/w) saccharide solution. To increase the ratio of α-D-glucosyl α-D-galactoside in the saccharide solution, "XT-1016™", Na-form, with four percents as a bridging degree, an alkali-metal-form strong acidic cation exchange resin commercialized by Rohm & Haas Japan Corporation, Tokyo, Japan, was suspended in water and packed in four stainless steeled jacketed-columns, three centimeters in diameter and one meter in length. The columns were cascaded in series to give total depth of about four meters. While keeping the column temperature at 40° C., the saccharide solution was fed to the columns in a volume of five percents (v/v) to the resin and fractionated by feeding a hot water of 40° C. at an SV (space velocity) 0.15 to collect fractions rich in α-D-glucosyl α-D-galactoside. The fractions were concentrated into an about 85% (w/w) solution which was then transferred to a crystallizer, and cooled while mixing to crystallize α-D-glucosyl α-D-galactoside in the presence of a seed crystal of about one percent (w/w) of the powdery crystalline α-D-glucosyl α-D-galactoside monohydrate of the present invention. The crystals were separated from the massecuite by a basket-type centrifuge, and the obtained crystals were washed by spraying a small amount of water and drying the resultant to obtain a powdery crystalline α-D-glucosyl α-D-galactoside in a yield of about 10% to the material, d.s.b.

The product was a saccharide powder containing an about 99% (w/w) of a powdery crystalline α-D-glucosyl α-D-galactoside, d.s.b., and had a melting point of 119–123° C. Since the product is stable; and easily handlable; has a relatively-low moisture absorption; fine sweetness, appropriate viscosity, and moisture retention; and does not substantially show a reducing property, it can be used in compositions such as food products, cosmetics, medicated cosmetics, pharmaceuticals, goods for life, reagents, and products for chemical industries, and products for agriculture, forestry and fisheries as a sweetener, taste improving agent, stabilizer, growth promoting agent of *bifidobacterium*, and absorption promoting agent of minerals.

EXAMPLE A-2

A Powdery Crystalline α-D-glucosyl α-D-galactoside

A solution containing 5.0% (w/w) of trehalose, 5.0% (w/w) of D-galactose, and 5 mM sodium phosphate dihydrate was adjusted to pH 5.0, and admixed with 15 units/g trehalose of the purified trehalose phosphorylase prepared by the method in Experiment 1, followed by reacting at 60° C. for 72 hours. The reaction mixture was heated at 95° C. for 30 min to inactivate the enzyme, cooled to 45° C., adjusted to pH 7.5, admixed with 10 units/g solids of trehalase from *Bacillus* sp. T3, produced by Hayashibara Biochemical Laboratories, Inc., Okayama, Japan, and incubated at 45° C. for 24 hours. The resulting mixture was heated at 100° C. while keeping to alkaline of pH 10 or higher by admixing with sodium hydroxide, cooled, in a conventional manner decolored by an activated carbon, filtrated, desalted and purified by ion exchanged resins with H- and OH-forms, and further concentrated into an about 45% (w/w) saccharide solution. To increase the ratio of α-D-glucosyl α-D-galactoside in the saccharide solution, the saccharide solution was fractionated by a column chromatography by using an alkali metal form strong acidic cation exchange resin described in Example A-1 to collect fractions rich in α-D-glucosyl α-D-galactoside. The fractions were concentrated into an about 85% (w/w) solution which was then transferred to a crystallizer, cooled while mixing in the presence of a seed crystal of about two percents of crystalline α-D-glucosyl α-D-galactoside monohydrate to obtain a massecuite with a crystallizing yield of about 10%. The massecuite was sprayed from a nozzle on a dried tower at a relatively-high pressure of 150 kg/cm². At the same time, a hot wind with a temperature of 80° C. was blown from the upper of the dried tower, and a crystalline powder was collected on a gauze conveyer for a transfer, and taken out by gradually transferring to outside of the dried tower while blowing a warm wind with a temperature of 40° C. from under the conveyer. The powder was packed to an aged tower, and crystallized and dried by aging for 10 hours while blowing a warm wind to obtain a powdery crystalline α-D-glucosyl α-D-galactoside in a yield of about 12% to the material, d.s.b.

The product was a saccharide powder containing an about 98.0% (w/w) of a powdery crystalline α-D-glucosyl α-D-galactoside, d.s.b., and had a melting point of about 119–123° C. and an endothermic peak in a range of about 118–138° C. in a DSC analysis. Since the product is stable; easily handlable; has a relatively-low moisture absorption, fine sweetness, appropriate viscosity, and appropriate moisture retention; and does not substantially show a reducing property, it can be used in compositions such as food products, cosmetics, medicated cosmetics, pharmaceuticals, goods for life, reagents, and products for chemical industries, and products for agriculture, forestry and fisheries as a sweetener, taste improving agent, stabilizer, growth promoting agent of *bifidobacterium*, and absorption promoting agent of minerals.

EXAMPLE A-3

A Powdery Saccharide Composition Comprising Crystalline α-D-glucosyl α-D-galactoside A solution containing 4% (w/w) of trehalose, 6% (w/w) of D-galactose, and 5 mM sodium phosphate dihydrate was adjusted to pH 5.0, and admixed with 20 units/g trehalose of a purified trehalose phosphorylase prepared by the method in Experiment 1, followed by reacting at 60° C. for 72 hours. The reaction mixture was heated at 95° C. for 30 min to inactivate the enzyme, cooled to 45° C., adjusted to pH 7.5, admixed with 20 units/g solids of trehalase from *Bacillus* sp. T3, produced by Hayashibara Biochemical Laboratories, Inc., Okayama, Japan, incubated at 45° C. for 24 hours, and cooled to 27° C. The resulting mixture was admixed with a commercialized baker's yeast in an amount of 10% by wet weight to the solid, incubated at 27° C. for 12 hours, while controlling the pH to 5–6 by using 1 M sodium hydroxide, to assimilate D-glucose. The resulting mixture was centrifuged to remove the cells, and the supernatant was in a conventional manner decolored with an activated carbon, filtrated, desalted, and purified by ion exchanged resins in H- and OH-forms, and further concentrated into an about 45% (w/w) saccharide solution. To increase the ratio of α-D-glucosyl α-D-galactoside in the saccharide solution, the saccharide solution was fractionated by a column chromatography by using an alkali metal form strong acidic cation exchange resin described in Example A-1 to fractions rich in α-D-glucosyl α-D-galactoside. The fractions were concentrated into an about 85% (w/w) solution which was then transferred to a crystallizer, cooled while mixing in the presence of a seed crystal of about one percent (w/w) of crystalline α-D-glucosyl α-D-galactoside monohydrate, transferred to a container, and left at 25° C. for five days to crystallize and solidify α-D-glucosyl α-D-galactoside. The obtained block was disrupted by a crusher and dried to obtain a powdery saccharide composition containing crystalline α-D-glucosyl α-D-galactoside in a yield of about 13% to the material, d.s.b.

The product was a saccharide powder containing an about 88.0% (w/w) crystalline α-D-glucosyl α-D-galactoside, d.s.b., and had an endothermic peak in a range of about 118–138° C. in a DSC analysis. This agreed with the character of the crystalline α-D-glucosyl α-D-galactoside of the present invention with a melting point of 119–123° C. Since the product is stable; easily handlable; has a relatively-low moisture absorption, fine sweetness, appropriate viscosity, and appropriate moisture retention; and does not substantially show a reducing property, it can be used in compositions such as food products, cosmetics, medicated cosmetics, pharmaceuticals, goods for life, reagents, and products for chemical industries, and products for agriculture, forestry and fisheries as a sweetener, taste improving agent, stabilizer, growth promoting agent of *bifidobacterium*, and absorption promoting agent of minerals.

EXAMPLE A-4

A Powdery Saccharide Composition Comprising Crystalline α-D-glucosyl α-D-galactoside A solution containing 10% (w/w) of trehalose, 5% (w/w) of D-galactose, and 5 mM sodium phosphate dihydrate was adjusted to pH 5.0, and admixed with 30 units/g trehalose of a purified trehalose phosphorylase prepared by the method in Experiment 1, followed by reacting at 60° C. for 90 hours. The reaction mixture was heated at 95° C. for 30 min to inactivate the enzyme, cooled to 45° C., adjusted to pH 7.5, admixed with 20 units/g solids of trehalase from *Bacillus* sp. T3, produced by Hayashibara Biochemical Laboratories, Inc., Okayama, Japan, and incubated at 45° C. for 24 hours. The obtained reaction mixture was heated at 90° C. for 30 min to inactivate the enzyme, cooled, in a conventional manner decolored with an activated carbon, filtrated, desalted and purified by ion exchanged resins in H- and OH-forms, and further concentrated into an about 45% (w/w) saccharide solution. To increase the ratio of α-D-glucosyl α-D-galactoside in the saccharide solution, the saccharide solution was fractionated by a column chromatography by using an alkali metal form strong acidic cation-exchange resin described in Example A-1 to collect fractions rich in α-D-glucosyl α-D-galactoside. The fractions were in a conventional manner decolored with an activated carbon, filtrated, desalted, and purified by ion exchanged resins in H- and OH-forms, dried in vacuo, and disrupted to obtain a powder containing an amorphous α-D-glucosyl α-D-galactoside. The obtained powder was spread on an aluminum container, left at 25° C. at a relative humidity of 60% for five days in a temperature and moisture controlling room, and crystalline α-D-glucosyl α-D-galactoside to obtain a powdery saccharide composition containing crystalline α-D-glucosyl α-D-galactoside in a yield of about 20% to the material, d.s.b.

The product was a saccharide powder containing about 70% (w/w) crystalline α-D-glucosyl α-D-galactoside, d.s.b., and had an endothermic peak in a range of about 118–138° C. in a DSC analysis. This agreed with the character of the crystalline α-D-glucosyl α-D-galactoside of the present invention with a melting point of 119–123° C. Since the product is easily handlable; and has a relatively-low moisture absorption, fine sweetness, appropriate viscosity, and moisture retention; it can be used in compositions such as food products, cosmetics, medicated cosmetics, pharmaceuticals, goods for life, reagents, and products for chemical industries, and products for agriculture, forestry and fisheries as a sweetener, taste improving agent, stabilizer, growth promoting agent of *bifidobacterium*, and absorption promoting agent of minerals.

The following Example B explains many compositions containing the crystalline α-D-glucosyl α-D-galactoside or the saccharide composition comprising the same of the present invention.

EXAMPLE B-1

Sweetener

To one part by weight of the powdery crystalline α-D-glucosyl α-D-galactoside obtained in Example A-2 was added 0.05 part by weight of "α-G SWEET™" (α-glycosylstevioside commercialized by Toyo Sugar Refining Co., Tokyo, Japan), and the resulting mixture was homogeneously mixed to produce a powdery sweetener. The product has a satisfactory sweetness and a 2-fold higher sweetening power of sucrose. The calorie of the product is about half of that of sucrose with respect to a sweetening power. Therefore, it can be preferably used as a low-caloric sweetener for low-caloric food products for fat persons and diabetics who are restricted to a reduced calorie intake. The product does not substantially form acids and insoluble glucans when dental carries-inducing microorganisms act on it, and this renders it useful for sweetening food products to prevent dental carries.

EXAMPLE B-2

Hard Candy

To twenty parts by weight of the saccharide composition containing crystalline α-D-glucosyl α-D-galactoside obtained in Example A-4 were added 80 parts by weight of a hydrogenated maltose syrup with moisture of 25% (w/w) and water with an adequate amount, and the mixture was then concentrated by heating under reduced pressure to give a moisture content of less than two percents (w/w), and the concentrate was mixed with one part by weight of citric acid and an adequate amount of a lemon flavor and food colors, followed by forming in a conventional manner the resultant into the desired product. The product is a hard candy which has a satisfactory mouth feel and satisfactory sweetness, less adsorb moisture, and substantially does not cause melting.

EXAMPLE B-3

Chewing Gum

To four parts by weight of the saccharide composition containing crystalline α-D-glucosyl α-D-galactoside obtained in Example A-3 were added three parts by weight of D-glucose and two parts by weight of a gum base melted by heating until it softened, and the mixture was further mixed with adequate amounts of a mint flavor, kneaded in a conventional manner by a roll, and formed to obtain the desired product. The product is a chewing gum having a satisfactory texture and taste.

EXAMPLE B-4

Chocolate

To 15 parts by weight of the saccharide composition containing crystalline α-D-glucosyl α-D-galactoside obtained in Example A-4 were mixed 40 parts by weight of a cacao paste, 10 parts by weight of a cacao butter, 10 parts by weight of sucrose, and 15 parts by weight of a milk powder, and the mixture was fed to a refiner to lower the granule size, placed in a conche, added 0.5 part by weight of lecithin, and kneaded at 50° C. over two days. Sequentially, the resulting mixture was poured into a mold and solidified to obtain the desired product. The product has no fear of fat-bloom and sugar-bloom, smoothly melts in the mouth, and has a satisfactory taste.

EXAMPLE B-5

Custard Cream

To 400 parts by weight of the saccharide composition containing crystalline α-D-glucosyl α-D-galactoside obtained in Example A-4 were mixed 500 parts by weight of corn starch, 500 parts by weight of maltose, and five parts by weight of salt, and the mixture was sufficiently mixed with sifting. The mixture was admixed with 1,400 parts by weight of egg, and gradually mixed with 5,000 parts by weight of a boiling milk. The resultant mixture was continued stirring under heating conditions, and the heating was stopped when the corn starch in the mixture was completely gelatinized to show the whole contents semitransparent, followed by cooling the resultant and adding thereto an adequate amount of a vanilla flavor to obtain the desired product. The product has a smooth surface and gloss as well as a mild taste and sweetness.

EXAMPLE B-6

"Uiro" (Sweet Rice Jelly)

To 70 parts by weight of the saccharide composition containing crystalline α-D-glucosyl α-D-galactoside obtained in Example A-4 were added 90 parts by weight of rice powder, 20 parts by weight of corn starch, 20 parts by weight of sucrose, one part by weight of "matcha" (powdered tea), and an adequate amount of water, and the mixture was kneaded. The resultant mixture was placed in a container and steamed up for 60 min to obtain an "uiro". The product has a satisfactory gloss, biting property, flavor and taste, as well as having a relatively-long shelf life because the retrogradation of the starch continued therein is well inhibited.

EXAMPLE B-7

"Bettara-Zuke" (a Kind of Whole Fresh Radish Pickles)

To one part by weight of the saccharide composition containing crystalline α-D-glucosyl α-D-galactoside obtained in Example A-3 were added three parts by weight of maltose, 0.05 part by weight of a product from licorice, 0.008 part by weight of malic acid, 0.07 part by weight of sodium glutamate, 0.03 part by weight of potassium sorbate, and 0.2 part by weight of pullulan, and the mixture was homogeneously mixed to obtain a "bettara-zuke-no-moto" (premix of a kind of whole fresh radish pickles). Thirty kilograms of fresh radishes were salted in a conventional manner, added sucrose, and soaked in a seasoning solution prepared by using four kilograms of the "bettara-zuke-no-moto" to obtain the desired product. The product has a satisfactory color, gloss, flavor, sweetness, and biting property.

EXAMPLE B-8

Beverage of Lactic Acid Bacteria

One hundred parts by weight of the saccharide composition containing crystalline α-D-glucosyl α-D-galactoside obtained in Example A-4, 175 parts by weight of a skim milk powder, and 50 parts by weight of "NYUKAOLIGO™", a high lactosucrose content powder commercialized by Hayashibara Shoji Inc., Okayama, Japan, were dissolved in 1,200 parts by weight of water. The resulting solution was sterilized at 65° C. for 30 min, then cooled to 40° C., in a conventional manner inoculated with 30 parts by weight of lactic acid bacteria as a starter, and incubated at 37° C. for eight hours to obtain the desired product with a satisfactory taste and flavor. Since the product contains oligosaccharide, it stably retains the lactic acid bacteria as well as promoting the growth.

EXAMPLE B-9

Soap

To 96.5 parts by weight of a neat soap obtained by, in a conventional manner, saponificating and salting-out a beef tallow and a coconut oil at a weight ratio of 4:1 were added 1.5 parts by weight of the saccharide composition containing crystalline α-D-glucosyl α-D-galactoside obtained in Example A-3, 0.5 part by weight of L-ascorbate 2-glucoside, 0.5 part by weight of sucrose, 0.5 part by weight of "α G Rutin", transglycosylated rutin commercialized by Toyo Sugar Refining Co. Ltd., Tokyo, Japan, one part by weight of maltitol, 0.0001 part by weight of kankoso 201 (pionin), and an adequate amount of a perfume. The mixture was homogeneously mixed, transferred to a mold, cooled, and solidified to produce a soap. The soap has a superior whitening effect and a satisfactory feeling after use without feeling skin dry, since it contains the saccharide composition comprising crystalline α-D-glucosyl α-D-galactoside.

EXAMPLE B-10

Bath Salt

To five parts by weight of the saccharide composition containing crystalline α-D-glucosyl α-D-galactoside obtained in Example A-4 were added 44 parts by weight of sodium sulfate, 14 parts by weight of sodium bicarbonate, seven parts by weight of sodium carbonate, 21 parts by weight of succinic acid, and an adequate amount of a lubricant, dye, and perfume. The mixture was homogeneously mixed and tabulated to obtain a bath salt. Since the bath salt contains the saccharide composition comprising crystalline α-D-glucosyl α-D-galactoside, it has a superior moisture-retaining ability and a blood stream promoting effect by a carbonic acid gas and a satisfactory feeling after use without feeling sticky.

EXAMPLE B-11

Hair Tonic

To eight parts by weight of the powdery crystalline α-D-glucosyl α-D-galactoside obtained in Example A-1 were added 50 parts by weight of ethanol, 1.5 parts by weight of polyoxyethylene (8) oleate, 0.1 part by weight of hinokitiol, one part by weight of glycyrrhizinic acid, 0.01 part by weight of kankoso 301 (takanal), five parts by weight of trehalose, 0.1 part by weight of ethylparaben, 0.05 part by weight of perfume, and an adequate amount of refined water. The mixture was in a conventional manner dissolved to obtain a hair tonic. Since the skin cream contains α-D-glucosyl α-D-galactoside, it has a satisfactory moisture-retaining ability and feeling after use without feeling sticky.

EXAMPLE B-12

Sunscreen Gel

One part by weight of "Aqupec™ HV505", a polyacrylate polymer commercialized by Sumitomo Seika Chemicals Co. Ltd., was dispersed in an adequate amount of refined water at about 55° C., cooled at 40° C. or lower, admixed with two parts by weight of L-ascorbate 2-glucoside dissolved in an adequate amount of water, and adjusted to pH 6.3 with 0.9 part by weight of potassium hydrate. The resultant mixture was admixed one part by weight of the powdery crystalline α-D-glucosyl α-D-galactoside obtained in Example A-2, six parts by weight of glycerol, two parts by weight of 1,3-butylene glycol, three parts by weight of dipropylene glycol, 1.3 parts by weight of sorbitol, 1.5 parts by weight of polyethylene glycol (400), and 3.1 parts by weight of 1,2-pentanediol, and the mixture was dissolved and filled a total weight to 100 parts with refined water to obtain a sunscreen gel. The sunscreen gel has a superior whitening effect. Since it contains α-D-glucosyl α-D-galactoside, it has a satisfactory moisture-retaining ability. Since its pH is kept to 5.9–7.0 with dipropylene glycol and polyethylene glycol, it is transparent and has a satisfactory feeling in spreading on skin and after use without feeling sticky and occurring a kink and grime after spreading observed in a general gel containing L-ascorbate 2-glucoside. Further, it is stable for a relatively-long shelf life without changing the pH, lowering viscosity, and coloring.

EXAMPLE B-13

Lotion

To two parts by weight of the powdery saccharide composition comprising crystalline α-D-glucosyl α-D-galactoside obtained in Example A-4 were added 0.2 part by weight of dipotassium glycyrrhizinate, 0.1 part by weight of citric acid, 0.3 part by weight of sodium citrate, five parts by weight of ethanol, 0.0001 part by weight of kankoso 201 (pionin), and 0.1 part by weight of ethylparaben, and the mixture was dissolved and filled a total weight to 100 parts with refined water to obtain a lotion. Since the lotion contains saccharide composition comprising α-D-glucosyl α-D-galactoside, is mild, and has a satisfactory moisture-retaining ability, it is used to prevent a skin damage and itch. It has a satisfactory feeling in spreading on skin and after use without feeling sticky.

EXAMPLE B-14

Rinse

To 2.5 parts by weight of liquid petrolatum were added 0.5 part by weight of myristic acid, 1.5 parts by weight of cetanol, three parts by weight of glycerol monostearate, one part by weight of di-polyoxyethylene 2-octyldodecyl ether N-lauroyl glutamate, and 0.5 part by weight of polyoxyethylene glyceryl monopyroglutamate monoisostearate, and the resultant mixture was mixed while heating to prepare "the mixture 1". To three parts by weight of the powdery saccharide composition comprising crystalline α-D-glucosyl α-D-galactoside obtained in Example A-3 were added three parts by weight of 1,3-buthylene glycol, 0.01 part by weight of kankoso 301 (takanal), 2.5 parts by weight of lauroyl-L-lysine, 0.5 part by weight of 1-arginine-ethyl-2-pyrrolidone-5-carboxylate, fatty acid ester, 0.5 part by weight of stearyl-trimethylammonium chloride, 0.1 part by weight of transglycosylated rutin, one part by weight of sodium pyrrolidonecarboxylate, one part by weight of an extract from Swertia Japonica Makino, and 74 parts by weight of refined water, and the mixture was mixed while heating to prepare "the mixture 2". The mixtures 1 and 2 were mixed and in a conventional manner emulsified to obtain a rinse. Since the rinse contains saccharide composition comprising α-D-glucosyl α-D-galactoside, it has a satisfactory moisture-retaining ability in spite of no glycerol and a satisfactory feeling after use without feeling sticky.

EXAMPLE B-15

Skin Cream

To four parts by weight of the powdery crystalline α-D-glucosyl α-D-galactoside obtained in Example A-1 were added two parts by weight of polyoxyethylene glycol monostearate, five parts by weight of glyceryl monostearate, self-emulsifying, two parts by weight of α-glycosyl rutin, one part by weight of liquid petrolatum, 10 parts by weight of glyceryl trioctanate, and an adequate amount of an antiseptic, and the mixture was in a conventional manner dissolved by heating. The resultant solution was admixed with five parts by weight of 1,3-butylene glycol and 66 parts by weight of refined water, and the resultant mixture was emulsified by a homogenizer and admixed with an adequate amount of a flavor under stirring conditions to obtain a skin cream. Since the skin cream contains α-D-glucosyl α-D-galactoside, it has a satisfactory moisture-retaining ability and spread and can be advantageously used as a sunscreen, skin-refining, and skin-whitening agent.

EXAMPLE B-16

Tooth Paste

To 12 parts by weight of the powdery crystalline α-D-glucosyl α-D-galactoside obtained in Example A-2 were added 45 parts by weight of calcium dihydrogen phosphate, 1.5 parts by weight of sodium lauryl sulfate, 25 parts by weight of glycerol, 0.5 part by weight of polyoxyethylene sorbitan laurate, 0.02 part by weight of saccharin, 0.05 part by weight of an antiseptic, and 16 parts by weight of water, and the mixture was mixed to obtain a dental paste. Since the dental paste contains α-D-glucosyl α-D-galactoside, it has an appropriate viscosity, a satisfactory feeling after use, gloss, and washing power.

EXAMPLE B-17

Eutrophic Agent for Intubation Feeding

A composition consisting of the following compositions was prepared: 80 parts by weight of the powdery crystalline α-D-glucosyl α-D-galactoside obtained in Example A-1, 190 parts by weight of powdered egg yolk, 209 parts by weight of a defatted milk, 4.4 parts by weight of sodium chloride, 1.85 parts by weight of potassium chloride, four parts by weight of magnesium sulfate, 0.01 part by weight of thiamine, 0.1 part by weight of sodium ascorbate, 0.6 part by weight of vitamin E acetate, and 0.04 part by weight of nicotinamide. Twenty-five grams aliquots of the composition were injected into moisture-proof laminated small bags and heat sealed to obtain the desired product. One bag of the product is dissolved in about 150–300 ml of water into a fluid food, and administered to nasal cavity, stomach, or intestine by intubation feeding to supplement energy to living bodies.

EXAMPLE B-18

Ointment for Curing an External Wound

To one part by weight of chlorhexidine gluconate solution were added 450 parts by weight of polyethylene glycol (400), three parts by weight of carboxyvinylpolymer, one part by weight of pullulan, and 400 parts by weight of isopropanol, and the mixture was mixed under a reduced pressure. The resultant mixture was admixed with 70 parts by weight of the powdery crystalline α-D-glucosyl α-D-galactoside obtained in Example A-1, three parts by weight of sodium hydrate, 77 parts by weight of refined water to obtain an ointment for curing an external wound with an appropriate spread and viscosity. Since the ointment contains α-D-glucosyl α-D-galactoside, it has a superior moisture-retaining ability and a satisfactory feeling in spreading without feeling viscosity, and can cure external wounds such as a cut, scratch, burn, dermatophytosis, and frostbite by spreading on a wound or covering a wound with a gauze spread the ointment.

The crystalline α-D-glucosyl α-D-galactoside and the saccharide composition containing the same of the present invention have a remarkably-low moisture absorption. Therefore, they have a relatively-low moisture absorption and a superior storage stability, and they substantially do not solidify, deliquesce, and lose fluidity. The crystalline α-D-glucosyl α-D-galactoside and the saccharide composition containing the same of the present invention can be advantageously used to many compositions such as food products, cosmetics, medicated cosmetics, pharmaceuticals, goods for life, reagents, products for chemical industries, and products for agriculture, forestry and fisheries, as a sweetener with a satisfactory sweetness, taste improving agent, quality improving agent, body-giving agent, viscosity controlling agent, moisturizer, gross giving agent, and nutrient supplying agent.

Further, they can be industrially produced with a large quantity and low cost according to the process for producing and converting the same of the present invention.

Thus, the present invention has a great influence on many fields such as food products, cosmetics, medicated cosmetics, pharmaceuticals, goods for life, reagents, products for chemical industries, and products for agriculture, forestry and fisheries.

While there has been described what is at present considered to be the preferred embodiments of the invention, it will be understood that various modifications may be made therein, and it is intended to cover in the appended claims all such modifications as fall within the true spirit and scope of the invention.

We claim:

1. A crystalline α-D-glucosyl α-D-galactoside, which has a melting point of 119–123° C.

2. The crystalline α-D-glucosyl α-D-galactoside of claim 1, which has peaks at diffraction (2θ) angles of at least 13.4°, 17.4°, 19.7°, and 22.3° on X-ray powder diffraction analysis using a CuK α-ray as an X-ray.

3. The crystalline α-D-glucosyl α-D-galactoside of claim 1 which has an endothermic peak in the range of about 118–138° C. on differential scanning calorimetry.

4. The crystalline α-D-glucosyl α-D-galactoside of claim 1, which is a crystalline α-D-glucosyl α-D-galactoside monohydrate.

5. A saccharide composition comprising the crystalline α-D-glucosyl α-D-galactoside of any one of claims 1 to 4.

6. A process for producing the crystalline α-D-glucosyl α-D-galactoside of any one of claims 1 to 4, which comprises:

(i) crystallizing the α-D-glucosyl α-D-galactoside of any one of claims 1 to 4 from its solution, and (ii) collecting the resulting crystal.

7. The process of claim 6, wherein said solution is in an aqueous solution form.

8. The process of claim 6 wherein said α-D-glucosyl α-D-galactoside is produced by reacting trehalose phosphorylase with D-galactose and β-D-glucose monophosphate and/or a salt thereof.

9. The process of claim 8, wherein said β-D-glucose monophosphate and/or said salt are produced by reacting trehalose phosphorylase to α,α-trehalose in the presence of an inorganic phosphoric acid and/or a phosphate thereof.

10. The process of claim 6, which comprises a step of increasing the purity of α-D-glucosyl α-D-galactoside by removing concomitant saccharides using one or more methods selected from the group consisting of alkaline treatment method, yeast fermenting method, and column chromatography method.

11. A process for producing the crystalline α-D-glucosyl α-D-galactoside of any one of claims 1 to 4 which comprises:

(i) drying a solution comprising α-D-glucosyl α-D-galactoside into an amorphous α-D-glucosyl α-D-galactoside (ii) converting the amorphous α-D-glucosyl α-D-galactoside to the crystalline α-D-glucosyl α-D-galactoside in the presence of moisture, and (iii) collecting the resulting crystal.

12. A process for converting an amorphous α-D-glucosyl α-D-galactoside to crystalline α-D-glucosyl α-D-galactoside, which comprises:

(i) drying a solution comprising α-D-glucosyl α-D-galactoside into an amorphous α-D-glucosyl α-D-galactoside, and
(ii) converting the amorphous α-D-glucosyl α-D-galactoside to the crystalline α-D-glucosyl α-D-galactoside of any one of claims 1 to 4 in the presence of moisture.

13. The composition of claim 5, which is in the form of a food product, cosmetic, medicated cosmetic, pharmaceutical, reagent, product for chemical industries, product for agriculture, product for forestry or product for fisheries.

* * * * *